United States Patent [19]

Okada et al.

[11] 4,210,440
[45] Jul. 1, 1980

[54] UREA DERIVATIVES, PROCESS FOR PREPARING THE SAME AND HERBICIDAL COMPOSITION CONTAINING THE SAME

[75] Inventors: Masanori Okada, Niiza; Yasushi Murakami; Hiromi Tomioka, both of Suginami; Norio Shirakawa, Iruma; Kunihiko Togashi, Yachiyo, all of Japan

[73] Assignee: Chugai Seiyaku Kabushiki Kaisha, Tokyo, Japan

[21] Appl. No.: 881,891

[22] Filed: Feb. 27, 1978

[30] Foreign Application Priority Data

Mar. 14, 1977 [JP] Japan .................................. 52-27077

[51] Int. Cl.$^2$ ..................... A01N 9/12; C07C 69/02
[52] U.S. Cl. ............................. 71/98; 260/453 RW
[58] Field of Search .................... 260/453 RW; 71/98

[56] References Cited

U.S. PATENT DOCUMENTS

| | | | |
|---|---|---|---|
| 3,697,572 | 10/1972 | Brown | 71/98 |
| 3,771,993 | 11/1973 | Brown | 71/98 |
| 3,790,364 | 2/1974 | Teach | 71/120 |
| 3,857,692 | 12/1974 | Feeny | 71/120 |

*Primary Examiner*—John M. Ford
*Assistant Examiner*—Robert C. Whittenbaugh
*Attorney, Agent, or Firm*—Browdy and Neimark

[57] ABSTRACT

A urea derivative represented by the formula

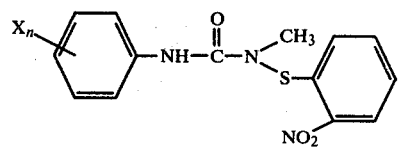

wherein X and n are defined hereunder, a process for preparing said derivatives and a herbicidal composition containing the same are disclosed.

21 Claims, No Drawings

UREA DERIVATIVES, PROCESS FOR PREPARING THE SAME AND HERBICIDAL COMPOSITION CONTAINING THE SAME

This invention relates to novel urea derivatives, a process for preparing the same and a herbicidal composition containing the same.

The inventors of this invention had prepared various compounds and investigated their activities for agricultural use. As a result, they found that a urea derivative represented by the formula (I) below had excellent herbicidal activity and they continued their study to complete this invention.

The urea derivative useful in this invention is represented by the formula

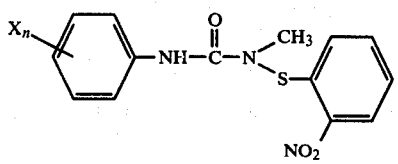

wherein X is halogen, lower alkyl, lower alkoxy, nitro or trifluoromethyl; n is an integer of from 1 to 3, provided, that if n is 2 or 3, X may represent any one of the members defined above.

According to this invention, the compounds represented by the formula (I) are prepared by reacting a compound represented by the formula

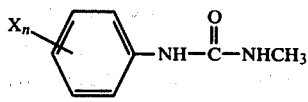

wherein X and n are as defined above with a compound represented by the formula

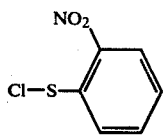

The reaction is effected by reacting the compound represented by the formula (II) with a compound represented by the formula (III) in a conventional organic solvent such as benzene, chloroform, ethyl acetate, dimethylformamide, dimethylsulfoxide, acetone or the like, in the presence of a suitable acid-acceptor for example an organic base such as triethylamine, pyridine, dimethylaniline or the like or an inorganic base such as sodium bicarbonate, potassium carbonate, sodium carbonate or the like at a temperature ranging from $-10°$ to $50°$ C., preferably from $10°$ to $30°$ for 1-12 hours while stirring to give the object compound in a high yield. The reaction mixture thus obtained is allowed to stand overnight and then is poured into ice-water and again allowed to stand until the oily substance becomes solid. The solid product is then recovered by filtration, washed with water, dried and recrystallized from an organic solvent such as ethyl acetate, or n-hexane or a mixture thereof to give a compound represented by the formula (I).

The compounds of this invention represented by the formula (I) have strong herbicidal activities on a broad spectrum of plants. Namely, the compounds exhibit strong herbicidal activities on both broad-leaf weeds and grassy weeds, for example, barnyard grass, crabgrass, waterhyssop, nutsedge, konagi (*monochoria vaginalis*), purslane and smartweed. The compounds have very low toxicity to fish. In addition to the above advantageous characteristics, they do not have any adverse effects such as phytotoxicity on desirable plants such as rice and corn.

In accordance with this invention, the active compound may be formulated in any conventional manner and applied to the field in any suitable dose, preferably 10–50 g/a, although the dose of the compound may vary depending on the species and infestation level of weeds to be controlled.

The compounds of this invention may be applied as herbicides in any conventional maner. One method for control of weeds comprises applying the composition to the soil before germination of weeds as a formulation for preemergence treatment. Another method is to apply a composition containing the active compound to the foliage of weeds at a suitable growth stage after germination. For control of weeds in paddy field, the compounds of this invention may be applied to the foliage of weeds or added to the water under flooding conditions. If the compounds are applied so as to directly contact the weed foliage, extremely high contact toxicity will be obtained whereby growth of weeds is completely controlled and the weeds are killed. However, even if the compounds are not directly contacted with the weed foliage, they will kill a considerable percentage and sufficiently control the growth of weeds.

Further, the compounds of this invention have good selectivity between weeds and desirable crops. That is, the application of the compounds of this invention provides sufficient control of any weeds infesting a field where desired crops such as rice or corn are growing without having any adverse effects on germination or growth of the crops.

The herbicidal composition of this invention can be formulated in any conventional manner and any suitable formulation can be selected for application depending upon the purpose for which it is intended.

The herbicidal composition of this invention is prepared by dissolving or dispersing one or more active compounds of this invention in a liquid carrier, or mixing them with or adsorbing them on a suitable solid carrier such as diluent and, if necessary, further adding one or more additives such as emulsifier, dispersing agent, suspending agent, spreader, penetrating agent, wetting agent and stabilizer to prepare a formulation such as oil, emulsion, solution, wettable powder, granule, dust, tablet or aerosol.

The solvents which are useful to formulate the herbicidal composition of this invention include alcohols such as ethanol and ethyleneglycol; ketones such as acetone and methyl ethyl ketone; ethers such as dioxane, tetrahydrofuran and cellosolves; aliphatic hydrocarbons such as gasoline, kerosene, fuel oil and machine oil; aromatic hydrocarbons such as benzene, toluene, xylene, naphtha and methylnaphthalene; organic bases such as pyridine and aldehydecollidine; amides such as dimethylformamide; esters such as ethyl acetate and butyl acetate; nitriles such as acetonitrile; and mixtures of two or more of them.

The solid diluents which are useful in this invention include vegetable powders such as soybean powder, flour and sawdust; mineral powders such as clays (for example, kaolin, bentonite and acid clay), talc, agalmotolite, diatom earth, silicate such as mica; alumina; sulfer powder; active carbon; or mixtures of two or more of them.

Emulsifiers which are useful in this invention include, for example, sulfated castor oil, nonionic emulsifier, alkylarylsulfonate and lignin sulfonate.

Spreaders which may be used in this invention include nonionic spreader, alkylsulfate, alkylarylsulfonate and mixtures of two or more of them. Instead of the spreader above, a pasty material such as casein, gelatin or starch may also be used.

The herbicidal composition of this invention can also comprise such additional substances as other herbicidal compounds, plant growth regulator, insecticide, nematocide, fungicide, synergists, flavor or fertilizer.

This invention will be further illustrated by the following Examples and Experiments. The parts in the Examples and Experiments are based on weight, unless otherwise indicated.

EXAMPLE 1

Production of Active Compounds (No. 3), N-(4-chlorophenyl)-N'-methyl-N'-(2-nitrophenylthio) urea N-4-chlorophenyl-N'-methyl urea (4.1 g) was dissolved in a mixture of dimethylformamide (20 ml) and pyridine (5 ml) and then 2-nitrophenylthiochloride (4.17 g) was added to and dissolved in the solution. After allowing the solution to stand overnight, it was poured into 200 ml of ice-water. The initial product was an oily product which solidified after a while. The solid product was separated by filtration, washed with water and dried. Recrystallization from a mixture of ethyl acetate and n-hexane gave 4.3 g of the object compound. (m.p.: 157°–158° C.)

Analysis: Calcd. for $C_{14}H_{12}N_3O_3SCl$: C, 49.78; H, 3.58; N, 12.44 (%). Found: C, 49.62; H, 3.37; N, 12.37 (%).

The compounds listed in Table 1 below were prepared as in Example 1. The reference number of the compound will be recited in the following Experiments and Examples.

Table 1

| Compound No. | Compound | melting point (°C.) |
|---|---|---|
| 1 | N-(2-chlorophenyl)-N'-methyl-N'-(2-nitrophenylthio) urea | 115.5–116.5 |
| 2 | N-(3-chlorophenyl)-N'-methyl-N'-(2-nitrophenylthio) urea | 173–174 |
| 3 | N-(4-chlorophenyl)-N'-methyl-N'-(2-nitrophenylthio) urea | 157–158 |
| 4 | N-(4-bromophenyl)-N'-methyl-N'-(2-nitrophenylthio) urea | 168.5–169.5 |
| 5 | N-(4-iodophenyl)-N'-methyl-N'-(2-nitrophenylthio) urea | 184–186 |
| 6 | N-(4-fluorophenyl)-N'-methyl-N'-(2-nitrophenylthio) urea | 116–117 |
| 7 | N-(2,3-dichlorophenyl)-N'-methyl-N'-(2-nitrophenylthio) urea | 137–138 |
| 8 | N-(3,4-dichlorophenyl)-N'-methyl-N'-(2-nitrophenylthio) urea | 169–170 |
| 9 | N-(2,4-dichlorophenyl)-N'-methyl-N'-(2-nitrophenylthio) urea | 167–168 |
| 10 | N-(2,4,6-trichlorophenyl)-N'-methyl-N'-(2-nitrophenylthio) urea | 200 |
| 11 | N-(3-trifluoromethyl-4-chlorophenyl)-N'-methyl-N'-(2-nitrophenylthio) urea | 204.5 |

Table 1-continued

| Compound No. | Compound | melting point (°C.) |
|---|---|---|
| 12 | N-(3-trifluoromethylphenyl)-N'-methyl-N'-(2-nitrophenylthio) urea | 151–152 |
| 13 | N-(4-nitrophenyl)-N'-methyl-N'-(2-nitrophenylthio) urea | 187–188 |
| 14 | N-(2,4-dinitrophenyl)-N'-methyl-N'-(2-nitrophenylthio) urea | 217–218 |
| 15 | N-(2,6-dimethylphenyl)-N'-methyl-N'-(2-nitrohenylthio) urea | 164 |
| 16 | N-(2,6-diethylphenyl)-N'-methyl-N'-(2-nitrophenylthio) urea | 144–145 |
| 17 | N-(4-methoxyphenyl)-N'-methyl-N'-(2-nitrophenylthio) urea | 123–124 |
| 18 | N-(2,5-diethoxyphenyl)-N'-methyl-N'-(2-nitrophenylthio) urea | 220–221 |

EXAMPLE 2

Preparation of Dust

Compound No. 8 (7 parts) was mixed with talc (93 parts) to give dust.

EXAMPLE 3

Preparation of Wettable Powder

Compound No. 3 (50 parts), sodium lignin sulfonate (1 part), polyoxyethylene alkylaryl ether (4 parts) and clay (45 parts) were mixed and pulverized to form wettable powder.

EXAMPLE 4

Preparation of Emulsion

Compound No. 13 (20 parts), polyoxyethylene alkylaryl ether (10 parts) and xylene (70 parts) were mixed to form an emulsion.

EXAMPLE 5

Preparation of Granules

Compound No. 9 (6 parts), bentonite (91 parts), carboxymethylcellulose (1.5 parts) and sodium alkylsulfate (1.5 parts) were kneaded and granulated in a conventional manner to form granules.

The activities of the compound of this invention were confirmed by the following Experiments.

EXPERIMENT 1

A field having such conditions that weeds such as crabgrass, purslane, nutsedge, goosefoot and smartweed would naturally infest was plowed to prepare the soil for seeding and divided into sections 10 m² area each. Then each section of the field was seeded with seeds of upland rice and corn plant and covered with soil.

Wettable powder formulated as in Example 3 which contained the active compound shown in Table 2 below was dispersed in water and sprayed on the soil surface in a dose of 25–50 g/a with a manual type portable sprayer. The herbicidal activity of each active compound was determined 35 days after treatment by measuring the weight of the infesting weeds and calculating the ratio of such weight to that in the untreated section (control section). At the same time, phytotoxicity to rice plant was also observed.

The results are shown in Table 2.

Table 2

| Compound No. | Dose (g/a) | % Weed Weight (based on untreated section) | | | | Phyto-toxicity to rice plant | Phyto-toxicity to corn plant |
|---|---|---|---|---|---|---|---|
| | | crab-grass | purs-lane | nut-sedge | smart-grass and others | | |
| 1 | 50 | 3 | 2 | 0.5 | 6 | none | none |
| 2 | 50 | 8 | 6 | 3 | 5 | " | " |
| 3 | 25 | 0 | 0 | 0 | 0 | " | " |
| 4 | 25 | 0 | 0 | 0 | 0 | " | " |
| 5 | 25 | 1 | 3 | 0 | 1 | " | " |
| 6 | 25 | 0.5 | 2 | 0 | 3 | " | " |
| 7 | 50 | 4 | 4 | 2 | 1 | " | " |
| 8 | 25 | 0 | 0 | 0 | 0 | " | " |
| 9 | 50 | 0 | 2 | 0 | 2 | " | " |
| 10 | 50 | 7 | 6 | 5 | 8 | " | " |
| 11 | 50 | 7 | 3 | 4 | 3 | " | " |
| 12 | 50 | 4 | 2 | 5 | 1 | " | " |
| 13 | 25 | 0 | 0 | 0 | 0 | " | " |
| 14 | 25 | 0 | 0.3 | 0.4 | 0 | " | " |
| 15 | 50 | 3 | 1 | 1 | 0.7 | " | " |
| 16 | 50 | 0.4 | 0.5 | 2 | 1 | " | " |
| 17 | 50 | 2 | 0.2 | 4 | 3 | " | " |
| 18 | 50 | 5 | 3 | 1 | 1 | " | " |
| C.H. | 50 | 7 | 10 | 8 | 18 | " | " |
| Untreated | — | 100 | 100 | 100 | 100 | — | — |

C.H.: control herbicide containing benthiocarb (S-p-chlorobenzyl diethylthiocarbamate)
Untreated: the section which has not been treated with any herbicide nor weeded.

EXPERIMENT 2

A paddy field having such conditions that weeds such as barnyard-grass, waterhyssop, nutsedge, toothcup, konagi (*monochoria vagialis*) would naturally infest was flooded with water, plowed and divided by plastic sheets into sections of 10 m² area each. Five days after young rice plant seedlings (2.5 leaves stage) were transplanted in the paddy field, granular composition formulated as in Example 5 was manually applied in water of the field in a dose of 25–50 g/a based on the active compound.

The herbicidal activity of each test compound was determined by measuring the weight of infesting weeds and calculating the ratio of the weight to that of weeds infesting the untreated section (control section). At the same time, phytotoxicity to rice plant was observed.

The results are shown in Table 3 below.

Table 3

| Compound No. | Dose (g/a) | % Weed Weight (based on untreated section) | | | | Phyto-toxicity to rice plant |
|---|---|---|---|---|---|---|
| | | barn-yard-grass | water-hyssop | konagi | nutsedge and others | |
| 1 | 50 | 6 | 3 | 4 | 1 | none |
| 2 | 50 | 2 | 6 | 2 | 4 | " |
| 3 | 25 | 0 | 0 | 0 | 0 | " |
| 4 | 25 | 2 | 0 | 0.5 | 0 | " |
| 5 | 25 | 0.2 | 4 | 0 | 0 | " |
| 6 | 25 | 0 | 3 | 3 | 2 | " |
| 7 | 50 | 1 | 0.3 | 2 | 4 | " |
| 8 | 25 | 0 | 0 | 0 | 0 | " |
| 9 | 50 | 4 | 7 | 1 | 2 | " |
| 10 | 50 | 8 | 9 | 5 | 5 | " |
| 11 | 50 | 4 | 3 | 2 | 4 | " |
| 12 | 50 | 4 | 0 | 2 | 0 | " |
| 13 | 25 | 0 | 0 | 0 | 0 | " |
| 14 | 25 | 0 | 0 | 0 | 0 | " |
| 15 | 50 | 0 | 4 | 3 | 2 | " |
| 16 | 50 | 3 | 2 | 6 | 0.3 | " |
| 17 | 50 | 2 | 0.4 | 0 | 3 | " |
| 18 | 50 | 4 | 2 | 0.6 | 0 | " |
| C.H. | 50 | 8 | 10 | 13 | 12 | " |
| untreated | — | 100 | 100 | 100 | 100 | — |

EXPERIMENT 3

Wagner pots with the surface area of 1/5000 are when the pots are filled with soil were filled with dry clayish loam, flooded with water at a level 0.5 cm depth above the loam surface and, then, cultivated. The pots were seeded with rice plant seeds on the surface of the soil submerged with water and covered with surface soil which had been picked up from resting paddy field and contained a large number of seeds of various weeds such as barnyardgrass, toothcup, waterstarwort, hardstem bulrush and the like. After seeding, the pots were placed in a greenhouse maintained at a temperature ranging from 20° to 30° C. to allow the rice plant and various weeds to germinate and grow.

A herbicidal composition which was an emulsion formulated as in Example 4 was sprayed on the water surface of pots by a portable glass sprayer in a dose of 25–50 g/a based on the active compound at 1.5 to 2 leaves stage in terms of rice plant and barnyard grass.

The herbicidal activity of each active compound was determined 21 days after the treatment by measuring the weight of infesting weeds and calculating the ratio of the weight to that of weeds in the untreated pot (control pot). At the same time, phytotoxicity to rice plant was also observed.

The results are shown in Table 4 below.

Table 4

| Compound No. | Dose (g/a) | % Weed Weight (based on untreated section) | | | | Phyto-toxicity to rice plant |
|---|---|---|---|---|---|---|
| | | barn-yard grass | tooth-cup | waterstar-wort | hard stem bulrush and others | |
| 1 | 50 | 4 | 2 | 0.3 | 3 | none |
| 2 | 50 | 3 | 1 | 3 | 0.4 | " |
| 3 | 25 | 0 | 0 | 0 | 0 | " |
| 4 | 25 | 0 | 0.2 | 1 | 0 | " |
| 5 | 25 | 2 | 1 | 5 | 3 | " |
| 6 | 25 | 0 | 0 | 0 | 0 | " |
| 7 | 50 | 7 | 0.6 | 3 | 2 | " |
| 8 | 25 | 0 | 0 | 0 | 0 | " |
| 9 | 50 | 3 | 4 | 3 | 1 | " |
| 10 | 50 | 2 | 5 | 0 | 2 | " |
| 11 | 50 | 4 | 3 | 4 | 7 | " |
| 12 | 50 | 6 | 2 | 4 | 1 | " |
| 13 | 25 | 0 | 0 | 0.2 | 0 | " |
| 14 | 25 | 0 | 0 | 0 | 0 | " |
| 15 | 50 | 2 | 2 | 0 | 1 | " |
| 16 | 50 | 7 | 0 | 3 | 0 | " |
| 17 | 50 | 8 | 4 | 0 | 0 | " |
| 18 | 50 | 4 | 3 | 1 | 0 | " |
| C.H. | 50 | 8 | 12 | 14 | 10 | " |
| untreated | — | 100 | 100 | 100 | 100 | — |

We claim:

1. An N-(substituted phenyl)-N'-methyl-N'-(2-nitrophenyl) urea represented by the formula

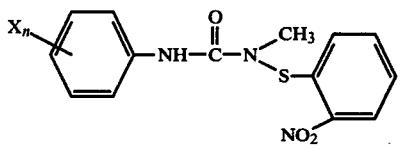

wherein X is halogen, lower alkyl, lower alkoxy, nitro or trifluoromethyl; n is an integer of from 1 to 3, provided that if n is 2 or 3, X may represent any one of the members defined above.

2. N-(2-Chlorophenyl)-N'-methyl-N'-2(nitrophenylthio) urea according to claim 1.

3. N-(3-Chlorophenyl)-N'-methyl-N'-(2-nitrophenylthio) urea according to claim 1.

4. N-(4-Chlorophenyl)-N'-methyl-N'-(2-nitrophenylthio) urea according to claim 1.

5. N-(4-Bromophenyl)-N'-methyl-N'-(2-nitrophenylthio) urea according to claim 1.

6. N-(4-Iodophenyl)-N'-methyl-N'-(2-nitrophenylthio) urea according to claim 1.

7. N-(4-Fluorophenyl)-N'-methyl-N'-(2-nitrophenylthio) urea according to claim 1.

8. N-(2,3-Dichlorophenyl)-N'-methyl-N'-(2-nitrophenylthio) urea according to claim 1.

9. N-(3,4-Dichlorophenyl)-N'-methyl-N'-(2-nitrophenylthio) urea according to claim 1.

10. N-(2,4-Dichlorophenyl)-N'-methyl-N'-(2-nitrophenylthio) urea according to claim 1.

11. N-(2,4,6-Trichlorophenyl)-N'-methyl-N'-(2-nitrophenylthio) urea according to claim 1.

12. N-(3-Trifluoromethyl-4-chlorophenyl)-N'-methyl-N'-(2-nitrophenylthio) urea according to claim 1.

13. N-(3-Trifluoromethylphenyl)-N'-methyl-N'-(2-nitrophenylthio) urea according to claim 1.

14. N-(4-Nitrophenyl)-N'-methyl-N'-(2-nitrophenylthio) urea according to claim 1.

15. N-(2,4-Dinitrophenyl)-N'-methyl-N'-(2-nitrophenylthio) urea according to claim 1.

16. N-(2,6-Dimethylphenyl)-N'-methyl-N'-(2-nitrophenylthio) urea according to claim 1.

17. N-(2,6-Diethylphenyl)-N'-methyl-N'-(2-nitrophenylthio) urea according to claim 1.

18. N-(4-Methoxyphenyl)-N'-methyl-N'-(2-nitrophenylthio) urea according to claim 1.

19. N-(2,5-Diethoxyphenyl)-N'-methyl-N'-(2-nitrophenylthio) urea according to claim 1.

20. A herbicidal composition containing as active ingredient, an N-(substituted phenyl)-N'-methyl-N'-(2-nitrophenylthio) urea represented by the formula

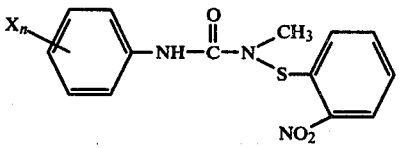

wherein X is halogen, lower alkyl, lower alkoxy, nitro or trifluoromethyl; n is an integer of from 1 to 3, provided, that if n is 2 or 3, X may represent any one of the members defined above.

21. A herbicidal composition according to claim 20 wherein said composition is in a formulation selected from the group consisting of oil, emulsion, wettable powder, granule, dust, tablet and aerosol.

* * * * *